United States Patent [19]

Mattsson

[11] 4,293,301

[45] Oct. 6, 1981

[54] DENTAL ABSORPTIVE PADS AND DISPENSING MEANS THEREFOR

[76] Inventor: Bengt Mattsson, Hässjövägen 4, Upsala, Sweden

[21] Appl. No.: 49,746

[22] Filed: Jun. 18, 1979

[30] Foreign Application Priority Data

Jun. 22, 1978 [SE] Sweden ................. 7807145

[51] Int. Cl.³ ............................................. A61C 5/14
[52] U.S. Cl. ................................. 433/136; 128/296; 225/51
[58] Field of Search ............... 433/136, 140; 128/296, 128/284, 290 R, 155, 290 P; 206/880, 824, 441, 440; 225/51, 52, 53, 84, 85, 87; 221/46

[56] References Cited

U.S. PATENT DOCUMENTS

| 1,293,484 | 2/1919 | Ley | 225/84 |
|---|---|---|---|
| 1,550,425 | 8/1925 | Burlew | 433/136 |
| 1,955,566 | 4/1934 | Schulz | 225/51 |
| 2,068,703 | 1/1937 | Powdermaker | 128/155 |
| 3,036,751 | 5/1962 | Bartschi | 225/51 |
| 3,122,140 | 2/1964 | Crowe, Jr. | 128/296 |
| 3,237,826 | 3/1966 | Ringholz et al. | 225/52 |
| 3,467,250 | 9/1969 | D'elia et al. | 206/820 |
| 3,468,030 | 9/1969 | Peyser et al. | 433/136 |
| 3,482,570 | 12/1969 | Schuster | 128/296 |
| 3,498,296 | 3/1970 | Gallagher | 128/284 |
| 3,583,558 | 6/1971 | Davis | 206/820 |
| 3,710,396 | 1/1973 | Tomlinson | 206/820 |
| 3,903,890 | 9/1975 | Mesek et al. | 128/296 |
| 4,027,672 | 6/1977 | Karami | 128/284 |

FOREIGN PATENT DOCUMENTS 217273 1/1958 Australia ................. 225/53

Primary Examiner—Gene Mancene
Assistant Examiner—John J. Wilson
Attorney, Agent, or Firm—Browdy and Neimark

[57] ABSTRACT

A dental absorptive pad having one thin layer of absorbent material with one thin non-absorbent layer on one face thereof, and with an overall shape with two peripheric rounded points separated by a central recess at a fore end, and one central rounded point opposite to and configurative with the central recess on a rear end. A plurality of such pads can be detachably connected together in a row, and a dispensing device for dispensing a reeled supply tape of such dental pads.

11 Claims, 8 Drawing Figures

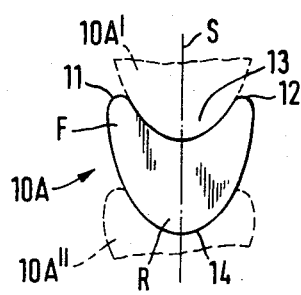
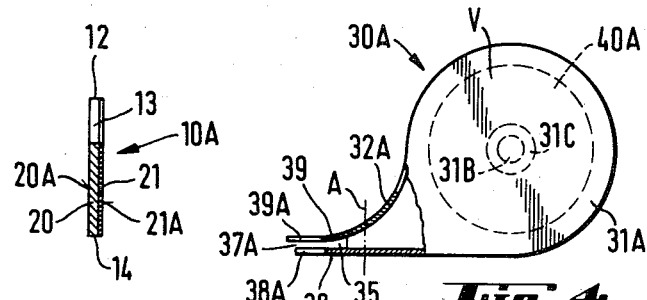
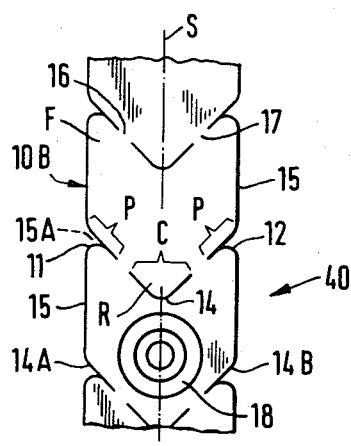
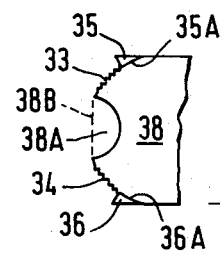
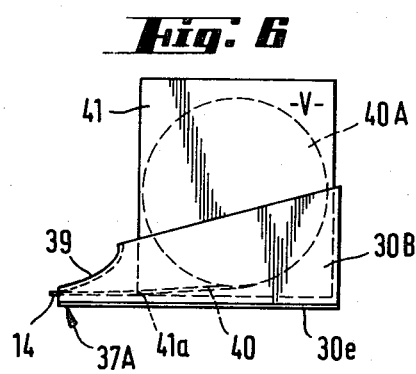
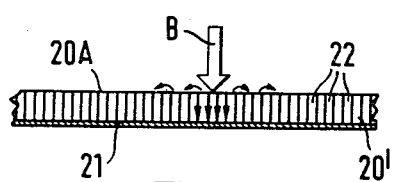
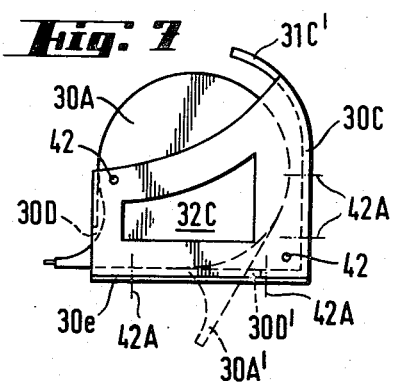

DENTAL ABSORPTIVE PADS AND DISPENSING MEANS THEREFOR

FIELD OF THE INVENTION

The present invention refers to dental absorptive pads adapted to be placed in the mouth of a patient to stem the saliva flow from the parotid gland during a dental operation or the like.

BACKGROUND OF THE INVENTION

One kind of such pads consisting of a thin sheet of absorbent solid material is described in the U.S. Pat. No. 3,468,030. The pads have a generally triangular shape with rounded corners (pear shape) and a size adapted to fit into the mouth between the teeth and the cheek. To the face of the pad which is turned towards the teeth is secured a thin layer of metal foil. Another kind of such pads is generally egg-shaped and instead of the attached metal foil, one surface of the pad is laminated with a rigid plastic film.

While these pads have proven to be a convenient and preferred substitute for the conventional cotton rolls used by dentists in the past for the absorption of saliva, they still have some disadvantages. With their straight or even convex fore edge they stick out of the corner of the wide open mouth of a patient and are an obstacle for the dentist's mirror. The term, "fore end" in the present description is meant to refer to the end located nearest to the corner of the mouth when the pad is used, and the term, "rear end", is meant to refer to the end located nearest the pharynx.

The pads must be individually removed from a staple comprising a plurality of loose pads piled one upon the other. Only the uppermost pad should at each instance be seized, e.g. by a pair of tweezers, but because of the flat shape of the pads, this is not always possible and even the underlying pad in the staple is often touched, which however is a hygienic disadvantage.

SUMMARY OF THE INVENTION

It is an object of the present invention to provide improved dental absorptive pads of the kind described. Another object of the invention is to provide a pad which can be produced more economically. Still another object is to provide improved storing and dispensing means for these pads.

According to the invention, a dental absorptive pad comprising at least one thin layer or sheet of absorbent material with at least one thin non-absorbent layer on one face thereof, has a fore edge or end with two peripheric protruding rounded points or corners separated by a central recess, and a rear edge or end with one central protruding rounded point or corner located opposite said central recess. Preferably, the circumferential shape of the rear end of the pad is configurative (congruent) with the circumferential shape of its fore end, so that the rear end of one pad can be closely inserted into the fore end of another pad.

BRIEF DESCRIPTION OF THE DRAWINGS

Other objects and features of the present invention will become apparent when studying the accompanying drawings which illustrate exemplary embodiments and wherein:

FIG. 1 is a plan view of a first embodiment of the present invention,

FIG. 2 is a cross-section along the plane S of FIG. 1,

FIG. 3 is a plan view of a plurality of pads according to a second embodiment, united to a supply tape or strip, FIG. 4 is a side view of a dispenser means in a first embodiment, FIG. 5 is a plan view at a larger scale of the fore portion of the dispenser of FIG. 4, FIG. 6 is a side view of a dispenser means in a second embodiment, FIG. 7 is a side view of a dispenser means in a third embodiment, and FIG. 8 is a diagramatical cross-section on a larger scale through an absorptive pad of the present invention in a further embodiment.

DESCRIPTION OF PREFERRED EMBODIMENTS

According to FIGS. 1 and 2, an absorptive pad 10A is generally heart-shaped having at its fore end F two peripheric rounded points or corners 11, 12 and a central recess or gap 13 between them, and, at the rear end R, a single, rounded point or corner 14 centrally located opposite the recess 13. The pad 10A has a front face 21A and a rear face 20A and comprises a layer 20 of an absorbent material, e.g. paper with a selected absorption rate and a film, layer or coating 21 of a non-absorbent transparent and smooth plastic material. By absorption rate is meant, in the present specification, the volume of liquid absorbed per unit of time, such as milliliters per second. The recess 13 has a circumferential shape which roughly corresponds to the contour line of an open mouth, i.e. to the average angle subtended by the lips of the patient when his mouth is wide open. Preferably, said shape is made configurative (congruent) with the shape of the single rounded point 14, so that individual pads may be chained together as indicated with the aid of two neighbouring pads 10A' and 10A", the terminal portions of which are shown in phantom. It will be appreciated that it is desirable that the absorptive pad have as large an area as possible, to last as long as possible before it is fully saturated. By combining, according to the present invention, the anatomically advantageous shape of the central recess 13 with the advantage achieved by its congruency with the central rounded point 14, a high degree of yielding may be achieved from raw material in sheet form from which the pads may be stamped out, as waste is largely reduced and consequently better economy is obtained in comparison e.g. with triangle-shaped or egg-shaped pads.

The shape of the side edges extending between the forward and rearward ends of the pad may vary to a certain extent, and in FIG. 3 is shown a second embodiment 10B where the side edges 15 are straight and parallel one with another. The overall shape according to FIG. 3 gives minimal waste when producing the pads from sheet or band material, thus largely improving the economy of production.

According to FIG. 3, an absorptive pad 10B has straight side edges 15 parallel one with another, connecting the fore and rear ends F, R thereof. It will be readily understood that with this embodiment, waste is further reduced as it is confined to the very small areas 15A as shown in phantom in FIG. 3, and thus the yield is further increased in comparison with the embodiment according to FIG. 1. In FIG. 3 is further demonstrated how the individual pads 10B may be chained one with another to form a supply tape or strip 40. At two locations, 16 and 17, intermediate a central zone C and two peripheral zones P of each pad ("central" and "peripheral" relative an axis of symmetry S) the pads are connected one with another in some known easily detachable manner, such as by means of fractural lines or linear perforations. It will be readily understood that the pads 10A of FIG. 1 may also be connected to form supply bands in the same manner, and that pads according to the present invention, disregarding their exact shape, may be easily produced by stamping-out whole supply tapes with hundreds of pads from raw material in sheet or band form.

On one of the pads of FIG. 3 a system of concentric rings 18 is shown, the purpose of which will be explained later on; in practice it would be present either on every, or on none of the pads of a given tape.

According to FIG. 4 a dispensing means for a supply band 40, wound into a supply reel 40A, has a storage chamber V defined by two parallel side walls 31A, of which only one is shown in the drawing, and a curved front wall 32A. The front wall 32A is made of a resilient or elastic material and is fixed to at least one of the side walls 31A along its whole periphery with the exception of a fore zone lying ahead of the line A. The fore zone of the front wall before the line A defines a resilient tongue 39 which constantly exercises a pressure in the downward direction in FIG. 4 and thus presses a supply band 40, dispensed from the supply reel 40A in the storage chamber V, against the bottom 38 of a dispensing nozzle 37A. This bottom 38, although it consists of the same material as the front wall 32A, and as a matter of fact is formed by a part of this front wall, is however rigid, because it is affixed to at least one of the side walls 31A until its front edge. The resilient tongue 39 which protrudes somewhat over the front edge of the bottom 38, and the terminal portion of the bottom 38 (ahead of the line A) define a dispensing nozzle 37A for the pads.

In FIG. 5 the front portion of the bottom 38 is shown in plan view and at a larger scale. Two peripheric stopping shoulders 35, 36A having internal contour lines 35, 35 substantially configurative with the contour lines 14A, 14B of the peripheric portions P (FIG. 3) of the pad, are provided on the bottom 38. Adjacent each stopping shoulder 35, 36, a tear-off zone 33, 34 with teeth and having contour lines essentially configurative with the fractural or perforational lines at the locations 16, 17, is provided. Between the two tear-off zones 33, 34 there is a central clearance 38A, so that in this zone the shape of the bottom differs from the shape of the rear end R of a pad. In the resilient tongue 39 there is provided a corresponding clearance 39A. In these two cooperating clearances 38A, 39A, which define a gripping zone of the dispensing nozzle, the central rounded point 14 of a pad will lie when the tape 40 is fed forward till it is stopped by the stopping shoulders 35, 36. The pad can thus easily be seized by a pair of tweezers and, overcoming the light pressure of the resilient tongue 39, be lifted over the shoulders 35, 36, and drawn out until the next pad is stopped by these shoulders. Then the pad held by the pair of tweezers is bent down and torn-off on the teethed tear-off zones 33, 34. At this moment, the central point 14 of the next pad already lies in the recesses 38A, 39A ready for dispensing. It will be readily understood that the clearances 38A and 39A may be replaced by a straight edge such as 38B, because even then the rounded point 14 will protrude. The resilient tongue 39 assures by its light downward pressure that any ensuing pad is stopped by the stopping shoulders 35, 36. The resilient tongue 39, the stopping shoulders 35, 36 and the tear-off zones 33, 34 define the essential features of the dispensing nozzle according to the present invention.

In FIG. 6 the dispenser means is divided into a separate supply and storage member in the shape of a box 41, wherein the supply reel 40A is contained, and a separate carrier member 30B provided with the dispensing nozzle 37A and adapted to receive the supply box 41 and to be itself conveniently fixed to a table plate or such, e.g. by means of an adhesive tape 30e. From the box 41 the tape 40 is fed through a narrow slot 41a and is then introduced into the dispensing nozzle 37A in the carrier member 30B. The carrier member 30B may thus remain fixed on a suitable place in the dental surgery and the box 41 is replaced by a new one when all the supply has been used up.

In FIG. 7 is shown a further modification of the dispenser means. A dispenser 30A according to FIG. 4, defining a separate storage member, is introduced into a carrier member 30C in which it can be placed in two different positions, viz. a first position shown in full lines, and a second position 30A' shown in phantom lines. The carrier member 30C has a curved resilient flap 31C which keeps the dispenser 30A in its place. In the carrier member 30C a plurality of screw holes 42 is provided, some of which are represented in the drawing only by their axes 42A. The carrier member may thus be fixed to a horizontal surface such as a table plate, or it may be fixed to a vertical surface with its rear wall or one of its side walls, because the screw holes 42 are provided in both side walls, and void spaces 32C in each side wall provide access to the screw holes in the other side wall. The carrier member can also be hung-up from beneath on a horizontal surface.

The carrier member 30C in FIG. 7 is shown without a dispensing nozzle of its own, as such a nozzle is arranged on the dispenser 30A itself. The carrier member 30C has two openings 30D, 30D' through any of which the dispensing nozzle may pass.

Absorptive pads according to the present invention may be produced from many known absorbent materials such as cotton, cellulose, paper etc. According to the present invention, it is particularly advantageous to treat the absorbent layer of the pads with an agent promoting its adhesivity to the mucous membrane of the mouth, and to select an absorption rate for this layer which is lower than the mean rate of discharge of saliva from the parotid which can be expected during a dental operation. In this way, active blocking of the saliva from the parotid gland, instead of only passive absorption of the saliva, is achieved.

The parotid gland has an orifice area of approximately 1 mm$^2$. The outflow of saliva therefrom is spread onto the whole surface, or more correctly into the whole volume, of the absorbent layer of the pad, and therefore it is also from the view of function important to save as great a portion thereof as possible from becoming waste. As soon as the whole pad is saturated with saliva, it must be replaced by a fresh one. By means of the adhesive treatment the pad "sticks" to the inner face of the cheek with a certain "plaster effect" and saliva is effectively stemmed in the parotid gland, which is a first factor delaying the necessity to replace a pad. Further, if the rate of absorption of the pad is lower than the rate at which saliva is produced in the parotid gland, the lifetime of each pad is further extended. A portion of the saliva will accumulate in the parotid gland and act with a certain small pressure on the pad, which however is retained by the adhesive agent on the inner face of the cheek.

It is known to produce, e.g. blotting paper, with selected absorptive capacity. In the present context it is however important that a reduction of the capacity of a material to take up a certain volume of liquid has not to be achieved, but only a reduction of the speed with which a greatest possible volume of liquid is sucked up by a given volume of the material (an extension of the time of full saturation).

In FIG. 3 is shown one preferred embodiment of an absorptive pad provided with an absorption delaying device, viz. the formerly named system of concentric rings 18 produced either by at least partial impregnation with a non-absorbent material having e.g. a composition essentially as a preparation distributed under the trademark "Squibb's Dental Orahesive" and manufactured by the company E. R. Squibb & Sons, Liverpool, or the like, and/or by mechanical squeezing (compression). The orifice of the parotid gland will be placed in the center of the system, and discharged saliva must first fill the space to the next barrier before it can, overcoming a certain resistance of the barrier, proceed further.

Another way to achieve a selectively reduced absorption rate is shown in FIG. 8. The absorbent layer 20' of the pad is composed of capillary fibres 22 which all are parallel one with another and oriented perpendicularly to the surfaces of the pad, so that saliva discharged from the parotid gland in the direction of arrow B is stopped at the opposed ends of the fibres 22 by the non-absorbent layer 21. Saliva can thus penetrate into neighbouring capillaries only along the rear face 20A of the pad adhering to the cheek, and possibly by osmosis through the walls of the capillaries.

Adhesive agents usable for plasters which can be put onto open wounds are already known, and may be used for the present purpose. The preparation "Squibb's Dental Orahesive" containing pectin, gelatin, sodium carboxymethyl-cellulose and polyisobutylene, proposed to produce the system of plural barriers, has also an adhesive effect and may therefore be used according to the present invention e.g. as a coating on the whole of the rear face 20A of the pad.

It will be now readily understood that an absorptive pad which absorbs saliva at the same rate as saliva is discharged from the parotid gland will be sooner saturated than a pad having the same absorptive capacity, but lower absorption rate. By using the adhesive agent, the "plaster effect" on the orifice of the parotid gland is achieved, and by reducing the absorption rate, the life time of each pad is extended. The pad may be provided with the adhesive agent either by impregnation, or only by surface treatment (coating).

Typically, the overall dimensions of a pad may be approximately 42×55 mm for adults, and 30×40 mm for children with a thickness in the order of 1 mm. To remove the pad from the mouth, a jet of water is directed towards it, or the patient fills his mouth with water.

The pads may further be impregnated or surface-treated with other agents as e.g. for increasing their affinity to the mucous membrane of the mouth (e.g. by increasing surface tension). It is however important that a patient's possible sensitivity towards any impregnating or surface-treatment agent be tested before application.

The non-absorbent layer is preferably made of transparent plastic material, which is known per se. Now however the additional advantage is gained that it can be easily observed how a pad with reduced absorption rate gradually gets impregnated from the center towards the periphery, and may thus in time be exchanged for a fresh one.

The supply reels 40A may be delivered hygienically packed in dispensers 30A according to FIG. 4 or 7 or in boxes 41 according to FIG. 6, or in any other suitable container from which they can be transferred into a dispenser.

One pad at a time is in the earlier described manner taken out from the dispenser with the aid of a pair of tweezers and is applied in the mouth of the patient with its rear face 20A turned towards the cheek and its rearward end R directed to the pharynx.

The invention can be modified in several ways, e.g. by adopting for the pads other shapes with two peripheric rounded points separated by a central recess, by disposing of the fractural impressions etc.

It will be appreciated that the dispensing nozzle according to the invention may also be used in connection with a supply tape not rolled up into a reel.

The carrier 30B can be provided with the same fixing means as the carrier 30C and vice versa.

One of the side walls of the dispenser 30A may be removable, e.g. by means of a central peg 31B (FIG. 4) thereon, inserted into a hollow hub 31C protruding from the other side wall, whereby refilling by new supply tapes is facilitated.

By the present invention a system for saliva absorption or blocking is proposed which enables economic production, hygienic packing and delivery, and easy and hygienic dispensing of the individual pads which in their turn are able to effectively hold dry the operational field in the mouth for an extended period of time.

What is claimed is:

1. A supply tape of dental absorptive pads comprising a series of said absorptive pads connected together end to end by score lines and in a detachable manner, each said pad having an inside face and an outside face, the inside face comprising a layer formed of an absorbent material and the outside face being formed of a layer of non-absorbent material, said inside layer formed of absorbent material constituting means to place against the parotid of a patient to lower the mean rate of discharge of saliva from the parotid and to absorb saliva therefrom;

each said pad having a fore end and a rear end, said fore end having two peripheric rounded points or corners separated by a central recess, said rear end having a central rounded point or corner generally complementary to and configurative with said fore end, whereby the central point of each pad is inserted into and separably attached to the central recess of a next adjacent pad.

2. A supply tape of dental absorptive pads comprising a series of said absorptive pads connected end-to-end, each said pad having a facing layer formed of an absorbent material and a facing layer of non-absorbent material, each said pad having a fore end having two peripheric rounded points or corners separated by a central recess, and a rear end having a central rounded point or corner whereby said rear end is generally complementary to and configurative with said fore end, the central point of each pad being inserted into and attached to the central recess of a next adjacent pad in a readily detachable manner at two locations between a central zone and two peripheric zones of said point and said recess.

3. A supply tape according to claim 2 wherein each pad has straight side edges parallel one with another connecting said fore and rear ends.

4. A supply tape according to claim 2 wherein in each dental absorptive pad said absorbent layer has a predetermined reduced absorption rate and is at least at its non-covered face treated with an agent enhancing its adhesitivity to the mucous membrane of the oral cavity.

5. The pad of claim 4, wherein the absorption rate is reduced by means of a system of barriers with increasing dimensions and incapsulated one into another.

6. The pad of claim 4, wherein the absorption rate is reduced by the said at least one absorbent layer consisting of capillary fibres parallel one with another and perpendicular to said front and rear faces.

7. A supply tape in accordance with claim 4, wherein said non-absorbent material is transparent.

8. A device useful for dental treatment, comprising a supply tape of dental absorptive pads including a series of said absorptive pads connected end to end, each said pad having a first facing layer formed of an absorbent material and a second facing layer of a non-absorbent material, each said pad having a fore end having two peripheric rounded points or corners separated by a central recess, and a rear end having a central rounded point or corner generally complementary to and configurative with said fore end, the central point of each pad being inserted into and attached to the central recess of a next adjacent pad in a relatively detachable manner, said supply tape being rolled in a reel; and means for dispensing said reeled supply tape of dental absorptive pads, said dispensing means comprising a storage chamber and a dispensing nozzle having a rigid bottom portion provided with two peripheric stop shoulders, two tear-off zones each adjacent one said shoulder, and a central gripping zone located intermediately of said two tear-off zones, and means to exercise pressure in a direction toward said bottom portion so that a said absorptive pad can be detached from said reel by aligning the attachment line between adjacent pads with said tear-off zones of said dispensing means and by grasping the pad to be removed and exerting downward pressure thereon.

9. The device of claim 8, wherein said dispensing means comprises a separate storage member defining said storage chamber, and a separate carrier member adapted to be affixed to a support and to readily accommodate said storage member.

10. The device of claim 9, wherein the dispensing nozzle is provided on the carrier member.

11. A device in accordance with claim 8, wherein adjacent pads are attached at two locations between a central zone and two peripheric zones of said point and said recess, and wherein said locations of attachment are aligned with said tear-off zones of said dispensing means.

* * * * *